United States Patent
Sun et al.

(10) Patent No.: US 10,415,881 B2
(45) Date of Patent: Sep. 17, 2019

(54) METHOD AND DEVICE FOR FREEZE-DRYING DRUG LIPOSOMES POWDER ASSISTED BY VARIABLE-FREQUENCY ALTERNATING-CURRENT ELECTRIC FIELD

(71) Applicant: South China University of Technology, Guangzhou (CN)

(72) Inventors: Dawen Sun, Guangzhou (CN); Lina Cheng, Guangzhou (CN); Zhiwei Zhu, Guangzhou (CN); Xin'an Zeng, Guangzhou (CN); Qijun Wang, Guangzhou (CN); Zi Zhang, Guangzhou (CN)

(73) Assignee: South China University of Technology, Guangzhou (CN)

( * ) Notice: Subject to any disclaimer, the term of this patent is extended or adjusted under 35 U.S.C. 154(b) by 190 days.

(21) Appl. No.: 15/548,054

(22) PCT Filed: Dec. 29, 2015

(86) PCT No.: PCT/CN2015/099639
§ 371 (c)(1),
(2) Date: Aug. 1, 2017

(87) PCT Pub. No.: WO2016/138790
PCT Pub. Date: Sep. 9, 2016

(65) Prior Publication Data
US 2018/0017324 A1  Jan. 18, 2018

(30) Foreign Application Priority Data
Mar. 3, 2015 (CN) .......................... 2015 1 0094656

(51) Int. Cl.
*F26B 3/34* (2006.01)
*F26B 7/00* (2006.01)
(Continued)

(52) U.S. Cl.
CPC .............. *F26B 7/00* (2013.01); *A61K 9/1277* (2013.01); *A61K 9/19* (2013.01); *F26B 5/041* (2013.01); *F26B 5/06* (2013.01); *F26B 20/00* (2013.01)

(58) Field of Classification Search
CPC ... F26B 5/06; F26B 7/00; F26B 20/00; A61K 9/19
(Continued)

(56) References Cited

U.S. PATENT DOCUMENTS

| | | | | |
|---|---|---|---|---|
| 2006/0137212 A1* | 6/2006 | Nomine | ............... | F26B 5/06 34/284 |
| 2010/0009008 A1* | 1/2010 | Watson | ............... | A61K 31/137 424/600 |
| 2014/0215845 A1* | 8/2014 | Corver | ............... | F26B 5/06 34/284 |

FOREIGN PATENT DOCUMENTS

| | | |
|---|---|---|
| CN | 1348085 A | 5/2002 |
| CN | 1987314 A | 6/2007 |

(Continued)

*Primary Examiner* — John P McCormack
(74) *Attorney, Agent, or Firm* — Hoffmann & Baron, LLP

(57) ABSTRACT

The present invention discloses a method for freeze-drying drug liposomes powder assisted by a variable-frequency alternating-current electric field, which includes the following steps: (1) preparing a drug-liposome suspension sample; (2) dehydrating the sample under a 1-10 kHz, 3-10 kV high-voltage alternating current; (3) freezing and drying the sample treated in step (2) at −20° C. to −40° C., under a 10-25 kHz, 0.2-1 kV high-voltage alternating current, until completion of the freezing process; and (4) heating and drying the sample in a vacuum until completion of subli- (Continued)

mation and desorption, and obtaining the drug liposomes freeze-dried powder. The present invention not only greatly shortens a freezing and drying time, but also controls a size of nuclei and ice crystals, further ensuring a quality of the freeze-dried powder.

14 Claims, 1 Drawing Sheet

(51) Int. Cl.
*F26B 5/06* (2006.01)
*F26B 20/00* (2006.01)
*A61K 9/127* (2006.01)
*A61K 9/19* (2006.01)
*F26B 5/04* (2006.01)

(58) Field of Classification Search
USPC .......................... 34/251, 250, 254, 255, 257
See application file for complete search history.

(56) References Cited

FOREIGN PATENT DOCUMENTS

| | | |
|---|---|---|
| CN | 101126596 A | 2/2008 |
| CN | 201059842 Y | 5/2008 |
| CN | 101526298 A | 9/2009 |
| CN | 102927793 A | 2/2013 |
| CN | 103988891 A | 8/2014 |
| CN | 104677057 A | 6/2015 |
| KR | 101342973 B1 | 12/2013 |
| TW | M416753 U | 11/2011 |
| WO | WO 2008/146005 A2 | 12/2008 |

* cited by examiner

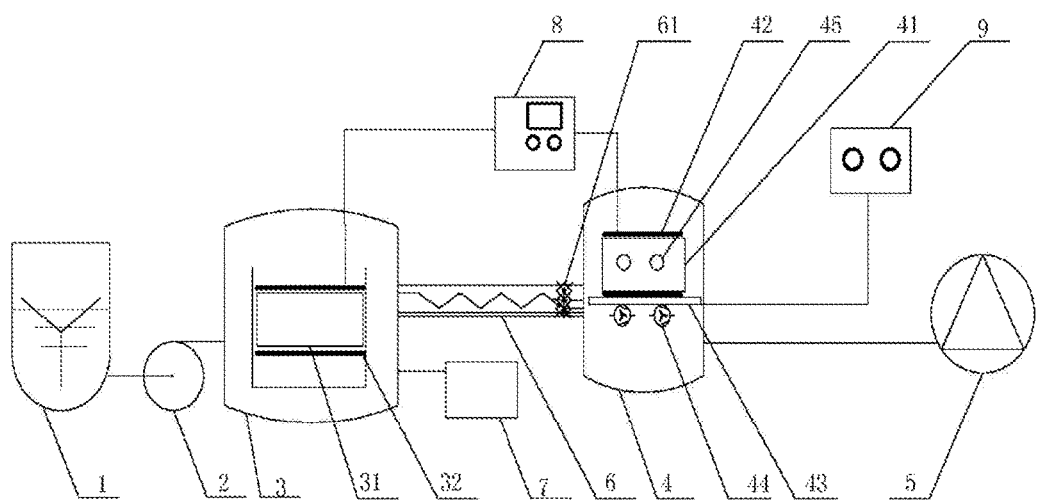

US 10,415,881 B2

METHOD AND DEVICE FOR FREEZE-DRYING DRUG LIPOSOMES POWDER ASSISTED BY VARIABLE-FREQUENCY ALTERNATING-CURRENT ELECTRIC FIELD

CROSS-REFERENCE TO RELATED APPLICATIONS

This application is the U.S. National Phase of International Patent Application No. PCT/CN2015/099639, filed on 29 Dec. 2015, which claims benefit of Chinese Patent Application No. 201510094656.9, filed on 3 Mar. 2015, the contents of which are incorporated herein by reference in their entirety.

FIELD OF THE INVENTION

The present invention relates to the field of the pharmaceutical preparation freeze-drying technology, and more particularly to a method and device for freeze-drying drug liposomes powder assisted by a variable-frequency alternating-current electric field.

BACKGROUND OF THE INVENTION

Vacuum freeze-drying, also known as freeze-drying, is a drying method, by which materials are frozen to below the eutectic point temperature and moisture in the materials is removed by sublimation in a low pressure state; it is especially suitable for extending the shelf life of biological preparations such as protein, vaccines and microbes, and improving the quality thereof. The general drying method is to change the moisture in a material from the liquid to the gaseous, while the freeze-drying method is to convert the moisture in the material from the liquid to the solid and then from the solid to the gaseous. Water freezing is an exothermic process, while ice sublimation is an endothermic process, so a freeze-drying system is mainly composed of three operations of refrigerating, heating and vacuuming.

Freezing is the shortest stage in the freeze-drying process, but it affects effects of several key steps such as sublimation, desorption and the freeze-drying throughout the process, such as shape and porosity of a cake, protein polymerization, and the like. Drying, as a long stage in the freeze-drying process, is divided into two small stages, a first drying stage (sublimation) and a second drying stage (desorption).

The size of the ice crystals in the freezing process determines the size of voids in the drying matrix, i.e., it determines the sublimation rate; however, the desorption rate is mainly determined by the specific surface area of the ice crystals. The bigger the ice crystals, the faster the heat transfer, and so the shorter the sublimation time; the larger the specific surface area, the easier the evaporation of the unfrozen water, i.e., the shorter the desorption stage. In general, a large degree of supercooling, i.e., there is a large gap between the equilibrium freezing point temperature and the nucleation temperature, will result in a lot of small ice crystals having a large specific surface area, that is, the first drying stage is slow, while the second drying stage is fast. However, a small degree of supercooling, i.e., the nucleation temperature is controlled to be close to the equilibrium freezing point temperature, will result in a lot of big ice crystals having a small specific surface area, that is, the sublimation is rapid and the desorption is slow. Controlling the nucleation step and removing different sublimation and desorption dynamic performances caused by the random nucleation temperature not only ensure the controllability of the drying process, but also further ensure the quality of the freeze-dried products. In short, the freezing stage affects the efficiency of the entire freeze-drying process and the quality of the products, such as protein stability.

Drying is the most energy-consuming stage in the freeze-drying process; since there is no convection in the vacuum environment, heat transfer and mass transfer are slow, and a common heating plate has a long heating cycle and large energy consumption. Semiconductor, which is a special material, can be used to increase and decrease temperature of 12 V direct current output fixed at heating and refrigerating commons and a commutation circuit composed of a relay, in a fast, timesaving and energy-saving way.

The biological preparations that are efficient but difficult to dissolve often use liposomes as a carrier to increase their clinical effects, and for such medicines a freeze-drying method is often used to obtain a freeze-dried powder, a freeze-dried needle and so on that have storage stability, high activity, and easy transport. At present, the commonly used auxiliary freeze-drying methods include the addition of a nucleation reagent in the freezing stage, and the novel ultrasonic treatment to control the nucleation temperature and the degree of supercooling. For the high activity of the biological medicines, the shorter the freeze-drying time, the better; the lower the water content of the finished products, the better; and the finer and more uniform the formed ice crystals, the better. Therefore, the prior art freeze-dried liposome medicines have the following drawbacks:

(1) An ordinary freeze-drying method cannot control the ice crystal growth in the freezing stage, that is, nucleation randomness, shape difference, and the like occur; besides, the size of ice crystals further affects the drying time, and the larger ice crystals may pierce cells in the freezing process to result in loss of drug efficacy. Inconsistent size of the ice crystals leads to unguaranteed uniformity of quality.

(2) For the freeze-drying method with an additional nucleation reagent, the addition of the nucleation reagent has complex parameters, difficult operation and high cost.

(3) The emerging ultrasound-assisted freeze-drying technology is prone to weakening the drug efficacy due to a lot of instantaneous latent heat caused by ultrasound; and the ultrasound function can be exhibited only in the presence of ultrasound media, which will greatly affect the design of an ultrasonic-freeze-drying integrative machine and bring great inconvenience; in addition, the noise caused by ultrasound is also very harsh.

(4) The conventional condensation-refrigeration system of a water sink is slow in heat transfer and needs long freezing time; the conventional heating system composed of a common heating plate needs long drying time, is energy consuming, and has a certain impact on the quality of the finished products.

(5) Neither a common nor a novel freeze-drying method can change the water content within a sample in the freeze-drying system, thereby reduce the freezing and drying time, and further control the nucleation and the quality of the finished products.

SUMMARY OF THE INVENTION

In order to overcome the above shortcomings and deficiencies of the prior art, a purpose of the present invention is to provide a method for freeze-drying drug liposomes powder assisted by a variable-frequency alternating-current electric field, which not only greatly shortens the freezing and drying time, but also controls the size of nuclei and ice crystals, further ensuring the quality of the freeze-dried powder.

Another purpose of the present invention is to provide a device for realizing the above method for freeze-drying drug liposomes powder assisted by a variable-frequency alternating-current electric field.

The purposes of the present invention are achieved by the following technical solution:

A method for freeze-drying drug liposomes powder assisted by variable-frequency alternating-current electric field is provided, including the following steps:

(1) preparing a drug-liposome suspension sample;

(2) dehydrating the sample under a 1-10 kHz, 3-10 kV high-voltage alternating current;

(3) freeze-drying the sample treated in step (2) at −20° C. to −40° C., under a 10-25 kHz, 0.2-1 kV high-voltage alternating current, until completion of the freezing process; and (4) heating and drying the sample in a vacuum until completion of sublimation and desorption, and obtaining the freeze-dried drug liposomes powder.

The water content of the drug-liposome suspension in step (1) is 40% to 80%.

The "dehydrating" in step (2) is specifically as follows: dehydrating until the water content of the sample is 18% to 35%.

The "until completion of the freezing process" in step (3) is specifically as follows: the temperature of the sample core reaches −20° C.

The "until completion of sublimation and desorption" in step (4) is specifically as follows: the temperature of the sample core reaches 20° C.

The device for freeze-drying drug liposomes powder assisted by a variable-frequency alternating-current electric field for realizing the above method for freeze-drying drug liposomes powder assisted by a variable-frequency alternating-current electric field includes a preparation bin, a metering pump, a dehydrator and a high/low-temperature treatment chamber sequentially connected to each other;

electrode plates are respectively provided above and below a sample tank in the dehydrator; electrode plates are respectively provided above and below a sample tank in the high/low-temperature treatment chamber; the electrode plates of the dehydrator and the high/low-temperature treatment chamber are connected to a high-voltage variable-frequency alternating-current power supply control cabinet;

the high/low-temperature treatment chamber is further connected to a vacuum pump; and the high/low-temperature treatment chamber is configured to perform freeze-drying and heat-drying processes on the sample.

A semiconductor refrigerating/heating sheet, provided below with a fan, is arranged under the sample tank of the high/low-temperature treatment chamber, which sample tank is provided with a wireless thermocouple probe.

The dehydrator is connected to the high/low-temperature treatment chamber through a screw pump.

The dehydrator is also connected to a waste tank.

The present invention, assisted by a high-voltage variable-frequency alternating-current electric field based on freeze-drying drug liposomes preparations, provides different high-voltage alternating-current treatment in the early stage of freezing process and subsequent freezing processes, respectively, so as to remove part of the water in the early period of freezing process and shorten the freezing and drying time; nucleation is inhibited in the freezing process, but the formed ice crystals are small, avoiding the mechanical damage caused by freezing and shortening the later drying time. Although high frequency and high voltage will produce some heat, the released latent heat is negligible compared to the semiconductor refrigerating effect in the refrigeration process; if the medicine has strict requirements on temperature in the dehydration process, a condensation circulator can be connected to the dehydrator to control the temperature; and the electric field has the characteristics of sterilization and can kill microorganisms, further ensuring the safety of biological preparations and avoiding the later sterilization of the freeze-dried powder.

Compared with the prior art, the present invention has the following advantages and benefits:

(1) Using the method of the present invention, the freeze-dried sample does not need to undergo a pre-freezing pretreatment step of a cryogenic refrigerator in a conventional freeze-drying process.

(2) Using the method of the present invention, a high-frequency AC power treatment is made in the early stage of freezing to result in a strong demulsification phenomenon, which greatly reduces the water content of the sample, such that the freeze-crystallizing time is greatly reduced, that is, the later drying sublimation stage will be greatly shortened correspondingly.

(3) Using the method of the present invention, a low-frequency AC power treatment is made in the freezing process, which delays the occurrence of nucleation; however, it is this inhibition of binding of the hydrogen bonds between water molecules that makes the formed ice crystals great in the quantity and small in the particle size. The larger specific surface area promotes the occurrence of the desorption stage in the drying process and shortens the drying time.

(3) Using the method of the present invention, the semiconductor is used for the refrigerating and heating system, saving the working time of the system for providing refrigerating and heating functions respectively with the condensate water sink and the heating plate, with the device simplified.

(4) Using the method of the present invention, the freeze-dried powder needs no sterilization, with the principle and effects here similar to those of sterilization by the pulsed electric field treatment.

(5) Using the method of the present invention, the freeze-drying time is greatly shortened, avoiding to some extent the problem of the loss of the biological medicine activity caused by the too long freeze-drying treatment time, further ensuring the effects and quality of the biological preparations.

BRIEF DESCRIPTION OF THE DRAWINGS

FIG. 1 is a schematic diagram showing the components of the device for freeze-drying drug liposomes powder assisted by a variable-frequency alternating-current electric field according to an example of the present invention.

DETAILED DESCRIPTION OF THE EMBODIMENTS

The present invention will be further described below in detail with reference to examples; however, the embodiments of the present invention are not limited thereto.

Example 1

FIG. 1 is a schematic diagram showing the device for freeze-drying drug liposomes powder assisted by a variable-frequency alternating-current electric field according to this example. As shown in FIG. 1, the device comprises a preparation bin 1, a metering pump 2, a dehydrator 3 and a high/low-temperature treatment chamber 4 sequentially connected to each other; electrode plates 32 are respectively provided above and below a sample tank 31 in the dehydrator 3; electrode plates 42 are respectively provided above and below a sample tank 41 in the high/low-temperature treatment chamber 4; the electrode plates 32, 42 are connected to a high-voltage variable-frequency alternating-current power supply control cabinet 8; the high/low-temperature treatment chamber 4 is further connected to a vacuum pump 5; and the high/low-temperature treatment chamber 4 is configured to perform freeze-drying and heat-drying processes on the sample.

A semiconductor refrigerating/heating sheet 43, connected with a semiconductor power supply control cabinet 9, is arranged under the sample tank 41 of the high/low-temperature treatment chamber 4; the semiconductor power supply control cabinet 9, including a refrigerating control system and a heating control system, is a refrigerating control system when connected forwardly, and a heating control system when connected reversely; a fan 44 is provided under the semiconductor refrigerating/heating sheet 43; and a wireless thermocouple probe 45 is provided on the sample tank 41. The dehydrator 3 is connected to the high/low-temperature treatment chamber 4 through a screw pump 6, which is provided with a valve 61. The dehydrator 3 is connected to a waste tank 7.

The outer wall of the preparation bin 1, the dehydrator 3, and the high/low-temperature treatment chamber 4 is double layered with an interlayer; the electrode plate is a stainless steel plate electrode, and includes two, upper and lower, symmetrical pieces close to the sample tank 31 of the dehydrator 3 and the sample tank 41 of the high/low-temperature treatment chamber 4 (the distance between the electrodes is about 11 cm); the semiconductor refrigerating/heating sheet 43 in the high/low-temperature treatment chamber 4 is close to the lower electrode; after the power is applied, there is a nonuniform electric field system in the high/low-temperature treatment chamber 4; the dehydrator 3 has a tempered glass window to facilitate observation of the electric dehydration phenomenon, thus allowing timely sampling and measurement of the water content of the sample with a moisture instrument; the wireless thermocouple probe 45 is used to measure the temperature change of the sample, i.e., to determine the freezing and heating time; the semiconductor refrigerating/heating sheet 43 is used to decrease and increase the temperature of the sample tank 41 during the freezing and heating stages, respectively. In addition, the size of the sample tank 41 of the high/low-temperature treatment chamber 4 can be freely changed according to actual needs; in the following examples, the size of the sample tank 31 of the dehydrator 3 is 40×15×10 cm (length× width×height), and the size of the sample tank 41 of the high/low temperature treatment chamber 4 is 30×15×10 cm (length×width×height). In the following examples, it is not necessary to connect a condensation circulator outside to the dehydrator 3, which can be determined according to actual needs.

The method for freeze-drying drug liposomes powder assisted by variable-frequency alternating-current electric field of this example comprises the following steps:

Weighing an appropriate amount of poloxamer 188 and polyethylene glycol-distearoyl phosphoethanolamine, adding an appropriate amount of Tween−80° C. to form an aqueous phase, and heating with a water bath to (70±5) ° C. to form an aqueous phase. Melting glyceryl behenate and cholesterol with a water bath at 75° C.; accurately weighing an appropriate amount of quercetin and soybean lecithin, and codis solving them in an appropriate amount of an acetone:ethanol (1:1) solvent to mix into an oil phase. Stirring and mixing the resulting aqueous phase and oil phase (v:v=1.5:1) in a preparation bin to form a water-in-oil emulsion system (having a water content of 75%) with a total volume of 5 L. Flowing into the sample tank of the dehydrator through a metering pump, treating under a 8 kV, 3 kHz high-voltage alternating current for 15 min (at this time the AC pulse duty factor was 35%), and demulsificating and dehydrating to a water content of 35%; at the same time of preparing the quercetin liposomes suspension, opening the semiconductor power supply control cabinet, connecting forwardly a refrigerating control system, and setting the temperature to −40° C.; sending the dehydrated sample with a pipe pump into the sample tank of the high/low-temperature treatment chamber (at this time the height of the sample was about 5 cm), closing the pipe switch, opening the vacuum pump, and treating under 25 kHz, 1 kV (at this time the AC pulse duty factor was 45%) until completion of the freezing process, that is, the temperature of the sample core was −20° C.; opening the semiconductor power supply control cabinet, connecting reversely the heating control system, and setting the temperature to 30° C., with the temperature of the sample core at 20° C. indicating completion of the drying stage; turning off the device, taking out the quercetin liposomes freeze-dried powder, and putting it into a sterile bottle.

The obtained quercetin liposomes freeze-dried powder had a water content of only 1%, uniform particle diameter, and pale yellow color; the enveloping rate was 90%; the hydrated redispersion was easy; the dose on the simulated biofilm surface was greater than that in the ordinary infusion; the treatment effect on an injury of the simulated mice was better than that of the quercetin technical; at the aspect of killing microorganisms, 4 orders of magnitude were reduced compared to the conventional freeze-dried powder, and 3 orders of magnitude were reduced compared to the novel microwave freeze-dried powder, within the scope of security; the freeze-drying time was shorter than the conventional freeze-drying time by 40 h, and shorter than the novel microwave freeze-drying time by 25 h.

Example 2

The method for freeze-drying drug liposomes powder assisted by variable-frequency alternating-current electric field of this example comprises the following steps:

Weighing a certain amount of breviscapine, and a respective appropriate amount of egg yolk lecithin, cholesterol, a surfactant and a stabilizer, adding a small amount of ethanol and dissolving the above materials in the ethanol by ultrasonic treatment, evaporating ethanol completely by decompressed rotatory evaporation, and hydrating with a hydrated medium containing mannitol and an antioxidant, thus obtaining the breviscapine liposomes suspension (having a water content of 55%) with a total volume of 3 L. Flowing into the sample tank of the dehydrator through a metering pump, treating under a 4 kV, 1 kHz high-voltage alternating current for 8 min (at this time the AC pulse duty factor was 40%), and demulsificating and dehydrating to a water content of 25%; at the same time of preparing the breviscapine liposomes suspension, opening the semiconductor power supply control cabinet, connecting forwardly a refrigerating control system, and setting the temperature to −25° C.;

sending the dehydrated sample with a pipe pump into the sample tank of the high/low-temperature treatment chamber (at this time the height of the sample was about 3.5 cm), closing the pipe switch, opening the vacuum pump, and treating under 15 kHz, 0.2 kV until completion of the freezing process, that is, the temperature of the sample core was −20° C.; opening the semiconductor power supply control cabinet, connecting reversely the heating control system, and setting the temperature to 25° C., with the temperature of the sample core at 20° C. indicating completion of the drying stage; turning off the device, taking out the breviscapine liposomes freeze-dried powder, and putting it into a sterile bottle.

The obtained breviscapine liposomes freeze-dried powder had a water content of only 0.8%, uniform particle diameter, and pale yellow color; the enveloping rate was 88%, and the hydrated redispersion was easy; the dose on the simulated biofilm surface was greater than that in the ordinary infusion; the treatment effect on an injury of the simulated mice was better than that of the breviscapine technical; at the aspect of killing microorganisms, 3 orders of magnitude were reduced compared to the conventional freeze-dried powder, and 2 orders of magnitude were reduced compared to the novel microwave freeze-dried powder, within the scope of security; the freeze-drying time was shorter than the conventional freeze-drying time by 20 h, and shorter than the novel microwave freeze-drying time by 10 h.

Example 3

Weighing a certain amount of docetaxel, and a respective appropriate amount of soy lecithin, cholesterol, a surfactant and mannitol, adding a small amount of ethanol and dissolving the above materials in the ethanol by ultrasonic treatment, evaporating ethanol completely by decompressed rotatory evaporation, and hydrating with a hydrated medium containing mannitol and an antioxidant, thus obtaining the docetaxel liposomes suspension (having a water content of 40%) with a total volume of 4 L. Putting in the sample tank of the dehydrator, treating under a 5 kV, 500 Hz high-voltage alternating current for 10 min (at this time the AC pulse duty factor was 50%), and demulsificating and dehydrating to a water content of 18%; at the same time of preparing the docetaxel liposomes suspension, opening the semiconductor power supply control cabinet, connecting forwardly a refrigerating control system, and setting the temperature to −30° C.; sending the dehydrated sample with a pipe pump into the sample tank of the high/low-temperature treatment chamber (at this time the height of the sample was about 5 cm), closing the pipe switch, opening the vacuum pump, and treating under 10 kHz, 0.5 kV until completion of the freezing process, that is, the temperature of the sample core was −20° C.; opening the semiconductor power supply control cabinet, connecting reversely the heating control system, and setting the temperature to 30° C., with the temperature of the sample core at 20° C. indicating completion of the drying stage; turning off the device, taking out the docetaxel liposomes freeze-dried powder, and putting it into a sterile bottle.

The obtained docetaxel liposomes freeze-dried powder had a water content of only 0.2%, uniform particle diameter, and milky white color; the enveloping rate was 85%, and the hydrated redispersion was easy; the dose on the simulated biofilm surface was greater than that in the ordinary infusion; the treatment effect on an injury of the simulated mice was better than that of the docetaxel technical; at the aspect of killing microorganisms, 2.5 orders of magnitude were reduced compared to the conventional freeze-dried powder, and 1.5 orders of magnitude were reduced compared to the novel microwave freeze-dried powder, within the scope of security; the freeze-drying time was shorter than the conventional freeze-drying time by 30 h, and shorter than the novel microwave freeze-drying time by 15 h.

The above examples are preferred embodiments of the present invention. However, the embodiments of the present invention are free from restriction of the examples, and any other modification, amendment, replacement, combination and simplification not departing from the spirit and principle of the present invention shall be the equivalent permutation, and all fall within the scope of protection of the present invention.

What is claimed is:

1. A method for freeze-drying drug liposomes powder assisted by variable-frequency alternating-current electric field is provided, wherein the method comprises the following steps:
   (1) preparing a drug-liposome suspension sample;
   (2) dehydrating the sample under a 1-10 kHz, 3-10 kV high-voltage alternating current;
   (3) freezing and drying the sample treated in step (2) at −20° C. to −40° C., under a 10-25 kHz, 0.2-1 kV high-voltage alternating current, until completion of the freezing process; and
   (4) heating and drying the sample in a vacuum until completion of sublimation and desorption, and obtaining the drug liposomes freeze-dried powder.

2. The method for freeze-drying drug liposomes powder assisted by variable-frequency alternating-current electric field according to claim 1, wherein the water content of the drug-liposome suspension in step (1) is 40% to 80%.

3. The method for freeze-drying drug liposomes powder assisted by variable-frequency alternating-current electric field according to claim 1, wherein the dehydrating in step (2) is specifically as follows: dehydrating until the water content of the sample is 18% to 35%.

4. The method for freeze-drying drug liposomes powder assisted by variable-frequency alternating-current electric field according to claim 1, wherein the until completion of the freezing process in step (3) is specifically as follows: the temperature of the sample core reaches −20° C.

5. The method for freeze-drying drug liposomes powder assisted by variable-frequency alternating-current electric field according to claim 1, wherein the until completion of sublimation and desorption in step (4) is specifically as follows: the temperature of the sample core reaches 20° C.

6. A device for freeze-drying drug liposomes powder assisted by a variable-frequency alternating-current electric field for realizing the above method for freeze-drying drug liposomes powder assisted by a variable-frequency alternating-current electric field according to claim 1, wherein the device comprises:
   a preparation bin, a metering pump, a dehydrator and a high/low-temperature treatment chamber sequentially connected to each other;
   first electrode plates are respectively provided above and below a first sample tank in the dehydrator; second electrode plates are respectively provided above and below a second sample tank in the high/low-temperature treatment chamber; the first electrode plates and the second electrode plates are connected to a high-voltage variable-frequency alternating-current power supply control cabinet;
   the high/low-temperature treatment chamber is further connected to a vacuum pump; and the high/low-temperature treatment chamber is configured to perform freeze-drying and heat-drying processes on the sample.

7. The device for freeze-drying drug liposomes powder assisted by variable-frequency alternating-current electric field according to claim 6, wherein a semiconductor refrigerating/heating sheet, provided below with a fan, is arranged under the second sample tank of the high/low-temperature treatment chamber, which the second sample tank being provided with a wireless thermocouple probe.

8. The device for freeze-drying drug liposomes powder assisted by variable-frequency alternating-current electric field according to claim 6, wherein the dehydrator is connected to the high/low-temperature treatment chamber through a screw pump.

9. The device for freeze-drying drug liposomes powder assisted by variable-frequency alternating-current electric field according to claim 6, wherein the dehydrator is connected to a waste tank.

10. A device for freeze-drying drug liposomes powder assisted by a variable-frequency alternating-current electric field, the device comprising:
a preparation bin, a metering pump, a dehydrator and a high/low-temperature treatment chamber sequentially connected to each other, the high/low-temperature treatment chamber being configured to perform freeze-drying and heat-drying processes on a drug liposomes sample;
first electrode plates respectively provided above and below a first sample tank in the dehydrator;
second electrode plates respectively provided above and below a second sample tank in the high/low-temperature treatment chamber;
a vacuum pump connected to the high/low-temperature treatment chamber; and
high-voltage variable-frequency alternating-current power supply control cabinet connected to the first electrode plates and the second electrode plates and configured to assist with freeze-drying drug liposomes powder obtained from the drug liposomes sample using variable-frequency alternating-current electric field.

11. The device for freeze-drying drug liposomes powder assisted by variable-frequency alternating-current electric field according to claim 10, wherein the device comprises a semiconductor refrigerating/heating sheet under the second sample tank of the high/low-temperature treatment chamber, the semiconductor refrigerating/heating sheet provided below with a fan.

12. The device for freeze-drying drug liposomes powder assisted by variable-frequency alternating-current electric field according to claim 10, wherein the second sample tank is provided with a wireless thermocouple probe.

13. The device for freeze-drying drug liposomes powder assisted by variable-frequency alternating-current electric field according to claim 10, wherein the device comprises a screw pump that connects the dehydrator to the high/low-temperature treatment chamber.

14. The device for freeze-drying drug liposomes powder assisted by variable-frequency alternating-current electric field according to claim 10, wherein the device comprises a waste tank connected to the dehydrator.

* * * * *